US006190871B1

(12) United States Patent
Ho et al.

(10) Patent No.: US 6,190,871 B1
(45) Date of Patent: *Feb. 20, 2001

(54) IMMUNOREAGENTS REACTIVE WITH A CONSERVED EPITOPE OF HUMAN IMMUNODEFICIENCY VIRUS TYPE I (HIV-1) GP120 AND METHODS OF USE

(75) Inventors: David D. Ho, Chapaqua, NY (US); James E. Robinson, New Orleans, LA (US)

(73) Assignee: Cedars-Sinai Medical Center, Los Angeles, CA (US)

( * ) Notice: Under 35 U.S.C. 154(b), the term of this patent shall be extended for 0 days.

This patent is subject to a terminal disclaimer.

(21) Appl. No.: 09/267,941

(22) Filed: Mar. 11, 1999

Related U.S. Application Data

(63) Continuation of application No. 08/870,531, filed on Jun. 6, 1997, which is a continuation of application No. 07/701,129, filed on May 16, 1991, now Pat. No. 5,798,251, which is a continuation-in-part of application No. 07/530,850, filed on May 29, 1990, now abandoned.

(51) Int. Cl.[7] ........................ G01N 33/53; G01N 33/565; G01N 33/567; C12Q 3/00; C12Q 1/00
(52) U.S. Cl. .................................. 435/7.24; 435/3; 435/4; 435/5; 435/7.24; 435/325; 424/130.1; 424/134.1; 424/141.1; 424/147.1; 424/148.1
(58) Field of Search .................................. 435/7.24, 3, 4, 435/5, 7.21, 325; 424/130.1, 134.1, 141.1, 147.1, 148.1

(56) References Cited

U.S. PATENT DOCUMENTS 5,798,251 * 8/1998 Robinson ........................ 435/240.27

OTHER PUBLICATIONS

Sun et al.; Generation and characterization of monoclonal antibodies to the putative cd–4binding domain of human immunodeficiency virus type 1 gp120; Journal of Virology; vol. 63, No. 9; pp. 3579–3585, Sep. 1989.*

* cited by examiner

Primary Examiner—Jeffrey Stucker
Assistant Examiner—Brett Nelson
(74) Attorney, Agent, or Firm—Lyon & Lyon LLP

(57) ABSTRACT

The invention features immunoreagents which neutralize the Human Immunodeficiency Virus Type 1 (HIV-1) by binding to a novel conserved epitope of the HIV-1 gp120. These immunoreagents exhibit a broad neutralizing effect upon HIV attachment to host cells, and are therefore useful in the detection, prevention, amelioration and treatment of HIV disease, primarily AIDS (Acquired Immunodeficiency Syndrome) and ARC (AIDS Related Complex). More particularly, the invention relates to novel human monoclonal antibodies selectively reactive to a conserved conformation dependent determinant of the HIV-1 gp120, derivatives thereof, cell lines that produce these antibodies, and the use of the monoclonal antibodies and their derivatives for the detection, prevention, amelioration and treatment of HIV related disease.

1 Claim, 11 Drawing Sheets

FIG. 2

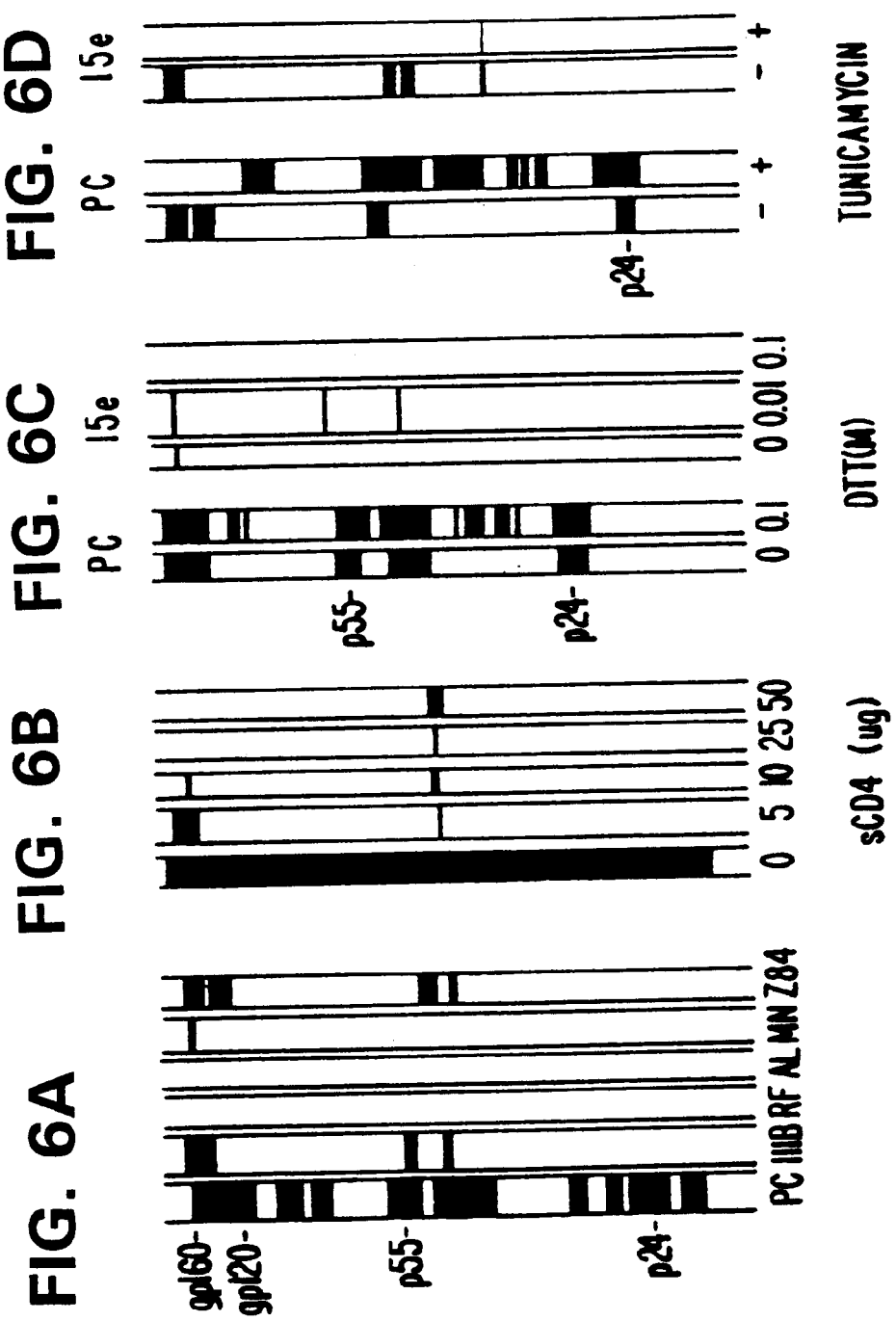

IMMUNOREAGENTS REACTIVE WITH A CONSERVED EPITOPE OF HUMAN IMMUNODEFICIENCY VIRUS TYPE I (HIV-1) GP120 AND METHODS OF USE

This present application is a continuation of co-pending U.S. application Ser. No. 08/870,531, filed Jun. 6, 1997, which is a continuation of U.S. application Ser. No. 07/701,129, filed on May 16, 1991, now U.S. Pat. No. 5,79,251, which is a continuation-in-part of U.S. application Ser. No. 07/530,850, filed May 29, 1990, now abandoned,

1. TECHNICAL FIELD

This invention is in the field of immunotherapy. Specifically, the invention relates to the development of antibodies and derivatives thereof, cell lines that secrete the antibodies, and their method of use in the prevention, detection, amelioration or treatment of HIV disease, primarily AIDS (Acquired Immunodeficiency Syndrome) and ARC (AIDS Related Complex).

2. BACKGROUND ART

Recent scientific inquiry has focused upon an extracellular glycoprotein of Human Immunodeficiency Virus Type 1 (HIV-1), namely gp120. This glycoprotein is believed to play a vital role in attachment of HIV-1 to a host cell, by binding specifically to the host cell's cellular receptor CD4 and therefore important for the development of an AIDS vaccine. However, the gene encoding gp120 is highly variable among different HIV-1 strains, including sequential isolates from the same patient (1–4). The greatest variability has been demonstrated in several hypervariable regions which are flanked by more conserved regions (3, 4).

In response to the AIDS virus, the host immune system will produce antibodies targeted against various antigenic sites, or determinants, of gp120. Some of those antibodies will have a neutralizing effect and will inhibit HIV infectivity. It is believed that this neutralizing effect is due to the antibodies' ability to interfere with HIV's cellular attachment. It is also believed that this effect may explain in part, the rather long latency period between the initial seroconversion and the onset of clinical symptoms.

Much of our present knowledge about which domains of gp120 are immunogenic has come from studies of antibodies raised in laboratory animals. It was first observed that a variety of animals immunized with purified or recombinant gp120 or gp160 developed strain specific neutralizing antibodies (5–7). Subsequently, polyclonal animal antisera raised to recombinant or synthetic peptides representing the third hypervariable domain (V3) of gp120 (covering amino acid residues 307–330) were found to manifest similar strain specific neutralizing activity. This observation identified the V3 domain as a major target of neutralization, at least in laboratory animals (8,9). The V3 hypervariable region is flanked by conserved cysteine residues which may form a disulfide bond and define a "loop" region containing the largely conserved sequence Gly-Pro-Gly in its center. Synthetic loop region peptides have been found to elicit the production of antibodies that neutralize only virus obtained from isolates from which the synthetic peptide was derived. Hence, the V3 loop induces type-specific neutralizing antibodies; but these antibodies do not account for the broad virus-neutralizing activity detected in the sera of most infected persons.

Several type-specific neutralizing murine monoclonal antibodies have been produced that bind to epitopes within the V3 domain (10–12), allowing precise mapping of these epitopes. Murine monoclonal antibodies have also been generated to epitopes associated with the CD4 binding region near the COOH terminal of gp120 (14–15); but the extent that this region is also involved in neutralization has not yet been conclusively established. Although the peptide sequence in this region is relatively well conserved, Lasky et al (14) detected minor sequence differences in several virus strains. This finding has raised the possibility that some antigenic variation may also occur within the CD4 binding domain.

Our present knowledge about which epitopes of gp120 stimulate humoral responses in chronically infected humans is much more limited. In contrast to the type-specific neutralizing activity of animal antisera, sera of HIV infected patients generally contain more broadly reactive, group specific neutralizing antibodies (15–17). Such broadly neutralizing antibodies may be directed against a conserved site on gp41, against antibodies specific for gag proteins (31–35), or possibly against conformational epitopes on gp120 (42). Nevertheless, several groups of investigators have also observed that some patient sera manifest distinct patterns of strain-restricted neutralizing activity when tested against a variety of strains (5,6,18,19). Moreover, patient antibodies that have undergone affinity purification to gp120 from one virus strain have been shown to possess type-specific neutralizing activity against that strain (6). These observations suggest that the multiplicity of antibodies commonly detected early in HIV-1 positive patient sera to variable epitopes may mask important later antibody responses to broad neutralization epitopes, which are believed to develop approximately six-twelve months after initial HIV seroconversion. Consequently, the need exists for the development of such agents with broad binding and neutralizing capabilities for the prevention, diagnosis and treatment of HIV and AIDS related infections. The present invention satisfies this need and provides related advantages as well.

The papers cited throughout this application are incorporated herein by reference.

3. DISCLOSURE OF THE INVENTION

We have discovered four (4) previously undescribed and unrecognized human monoclonal antibodies which exhibit binding affinity for a specific conserved antigenic determinant of gp120. Tests indicate this binding to be dependent upon the tertiary or non-linear structure of the glycoprotein, and is important for both HIV-1 neutralization and CD4 binding. In addition, and in part because of the unexpected and surprising potency with which HIV infectivity is neutralized by these monoclonal antibodies, we believe the HIV determinant to be located in the CD4 binding region of gp120.

a. Definitions

As used herein, the terms "immunoreagent," "immunoreagent equivalent" and "immunoreagent derivative" refer to antibodies, antibody fragments, antisera, antiidiotypes, polypeptides or derivatives thereof, whether human, hybrid, chimeric or recombinant, purified or produced by any method, whether conjugated to toxins to enhance immunotoxicity or other molecules to enhance immunogenicity, and the cell lines which produce the antibodies, which bind in an equivalent manner to gp120, have similar neutralization activity, or otherwise mimic this epitope, and their use for the prevention, diagnosis, treatment or amelioration of HIV related disease.

As used herein, references to "gp120 antigen," "gp120 antigenic determinant" and "epitope of HIV-1 gp120," refer to that portion of the HIV-1 virus which is capable of combining with antibodies and derivatives thereof, T cell receptors and immunoreagents which mimic T cell receptors, and which is capable of inducing an immune response.

As used herein, the terms "reactive" and "reactivity" refer to an ability of the immunoreagent to recognize, bind to and/or mimic an antigen, antigenic determinant and/or epitope.

b. Method of Production

Because epitopes recognized by immunized animals may differ from those that stimulate antibody responses in naturally infected humans, we have produced human monoclonal antibodies (HMabs) that represent immunogenic responses of chronically infected patients to gp120 antigens. This production incidentally has allowed more precise identification and characterization of both conserved and variant gp120 determinants recognized by the human immune system. These IgG HMabs were produced by B cell lines derived by EBV transformation of peripheral blood B lymphocytes obtained from three asymptomatic HIV-1 infected patients. However, these antibodies and derivatives thereof, can also be produced in animals or with the help of hybridoma methods (monoclonal antibodies in mice or monoclonal antibodies in humans) or in yeast, bacteria or mammalian cells by recombinant methods.

In particular, N70-1.5e, N70-1.7B, N70-2.1H and Y76-4.8D bind to a previously undescribed and unrecognized conformation dependent epitope on gp120, and exhibit surprisingly great potency for HIV neutralization. This epitope also appears to be responsible for inducing the broad HIV neutralizing and cellular binding inhibitory activity observed in HIV infected human sera.

Antibodies or equivalent structures, that bind to this site can be used to generate anti-idiotype antibodies. The anti-idiotypes will share certain three-dimensional features with the original antigen to which our antibodies and like molecules bind. Moreover, the anti-idiotypes immunologically mimic the HIV antigens, as they are readily generated from the claimed antibodies and like-molecules. Furthermore, the anti-idiotypes are relatively non-toxic to humans, and elicit an immune response in the same manner as the corresponding epitopes of the original antigens, yet without the accompanying viral threat to the patient. By challenging a patient's immune system with a judicious mixture of anti-idiotypes, a broad immune response can be induced to many variants of the HIV virus. This is known in the field of immunotherapy as active immunization, and is an area where this invention could find valuable potential. The antibody or equivalent immunoreagent could be covalently linked to a solid phase matrix for affinity purification, and the purified product, in admixture with an acceptable pharmaceutical excipient, used as an AIDS vaccine.

We specifically disclose human monoclonal antibody N70-1.5e (I5e) as the prototype antibody and the best mode of our invention at this time. However, it is to be understood that future embodiments with superior or more broad N70-1.5e-like characteristics may be discovered or generated, or other embodiments may be utilized without departing from the scope of the invention. In this regard, we also specifically disclose human monoclonal antibodies N70-1.7B, N70-2.1H and Y76-4.8D, generated subsequent to the discovery of N70-1.5e, which in preliminary experiments, appear to have N70-1.5e-like binding and neutralizing activity.

c. Application

The following suggested uses for the present invention are not intended to limit the scope of the invention, but rather provide a small window of understanding to illustrate its broad application and enormous potential.

As such, the antibodies and/or their derivatives could be used therapeutically in several different situations:

1. the prevention of HIV-1 infection in persons with acute exposure to HIV (e.g. needle sticks);
2. the prevention of vertical transmission to infants from HIV infected mothers;
3. passive immunotherapy of patients with established HIV infection; and
4. active immunotherapy of patients using a mixture of anti-idiotypes or equivalent immunoreagents.

These antibodies and/or their equivalent immunoreagents, in admixture with an acceptable pharmaceutical excipient, could therefore be useful in the development of a vaccine for AIDS, as well as in monitoring the retention of the conformational epitope in HIV-1 vaccines containing all or a portion of gp120.

In addition, these antibodies and/or their equivalent immunoreagents could be used in an immunoassay for diagnosing AIDS in a test sample from a human, and for monitoring antibody responses in AIDS vaccine recipients. The test sample for use in an immunoassay could be any one of whole blood, lymphatic fluid, serum, plasma, semen, saliva, and cerebral spinal fluid; and the presence of the AIDS virus infection could be indicated by the presence of gp120 antigen/immunoreagent complexes in the test sample.

For all such diagnostic, prophylactic and therapeutic uses, the monoclonal antibodies and/or their derivatives as well as other necessary reagents and appropriate devices and accessories may be provided in kit form. The kit can be prepared in a single container, individual bottles, bags, vials or other containers each having an effective amount of the immunoreagent for therapeutic or diagnostic use. This kit can comprise, for example, the immunoreagent in a single container, optionally as a lyophilized plug, and a container of solutions for reconstitution.

These immunoreagents could also be used to further elucidate the structure and function of various other gp120 determinants.

We therefore disclose and claim human monoclonal antibodies N70-1.5e, N70-1.7B, N70-2.H and Y76-4.8D and derivatives thereof, and the cell lines which produce the antibodies, which bind in an equivalent manner to gp120, and have similar neutralization activity, and their use for the prevention, diagnosis, treatment or amelioration of HIV related disease. However, those skilled in the art will readily appreciate modifications and changes in the procedures, compositions and methods of use set forth without departing from the scope and spirit of the invention. Moreover, other features and advantages of the present invention will become apparent from the following detailed description which illustrates the principles of the invention.

4. BRIEF DESCRIPTION OF THE DRAWINGS

The present invention will be described in connection with the accompanying drawings in which:

FIGS. 1A and 1B is a Western blot of HMab reactivity with two HIV-1 viral strains, IIIB and J62. The reactivity of four HMabs with strips in both panels is as follows: Lane 1, K24-3b, Lane 2, N70-2.3a, Lane 3 N70-1.5e, Lane 4, N70-1.9b. Lane 5 demonstrates the reactivity of sheep anti-HTLV-IIIB gp120.

FIG. 2 is a dot blot illustrating the reactivity of four HMabs with purified gp120 of strain J62, non-reduced recombinant LAV gp120, reduced recombinant LAV gp120, and nonreduced, heated LAV gp120.

FIG. 3 is a graphic representation of ELISA reactivity of K24-3b and N70-2.3a HMabs with Con-A immobilized gp120 from nine strains of HIV-1. Results are shown as the mean optical density (O.D.) reading from triplicate determinations. Standard deviation bars are shown. H72 is the code designation of an HIV-1 antibody positive control serum.

FIG. 4 is a graphic representation of ELISA reactivity of N70-2.3a, N70-1.5e, and N70-1.9b HMabs with Con-A immobilized gp120 from eight strains of HIV-1. Results are shown as single determinations.

FIGS. 5A and 5B illustrate the reactivity of K24-3b and N70-2.3a HMabs with Western blots prepared from eight independent HIV-1 strains. FIG. 5A represents the reactivity of K24-3b; and FIG. 5B represents the reactivity of N70-2.3a. The different strains are indicated by code numbers at the top of each blot lane; IIIB refers to HTLV-IIIB.

FIGS. 6A–6D represent serologic studies performed with HMab I5e against various HIV variants alone, or in combination with soluble CD4 (sCD4), dithiothreitol (DTT) and tunicamycin. In particular:

FIG. 6A represents I5e reactivity with diverse HIV-1 isolates: IIIB, RF, AL, MN and Z84; whereas PC is the positive control serum reacting with IIIB proteins.

FIG. 6B represents the competition between I5e and sCD4 for binding to 9p120/160 of HIV-1.

FIG. 6C represents that gp120 reduction by DDT eliminates I5e reactivity.

FIG. 6D represents that I5e reactivity with the envelope protein of HIV-1 is lost when glycosylation is inhibited by tunicamycin.

Figure 7:
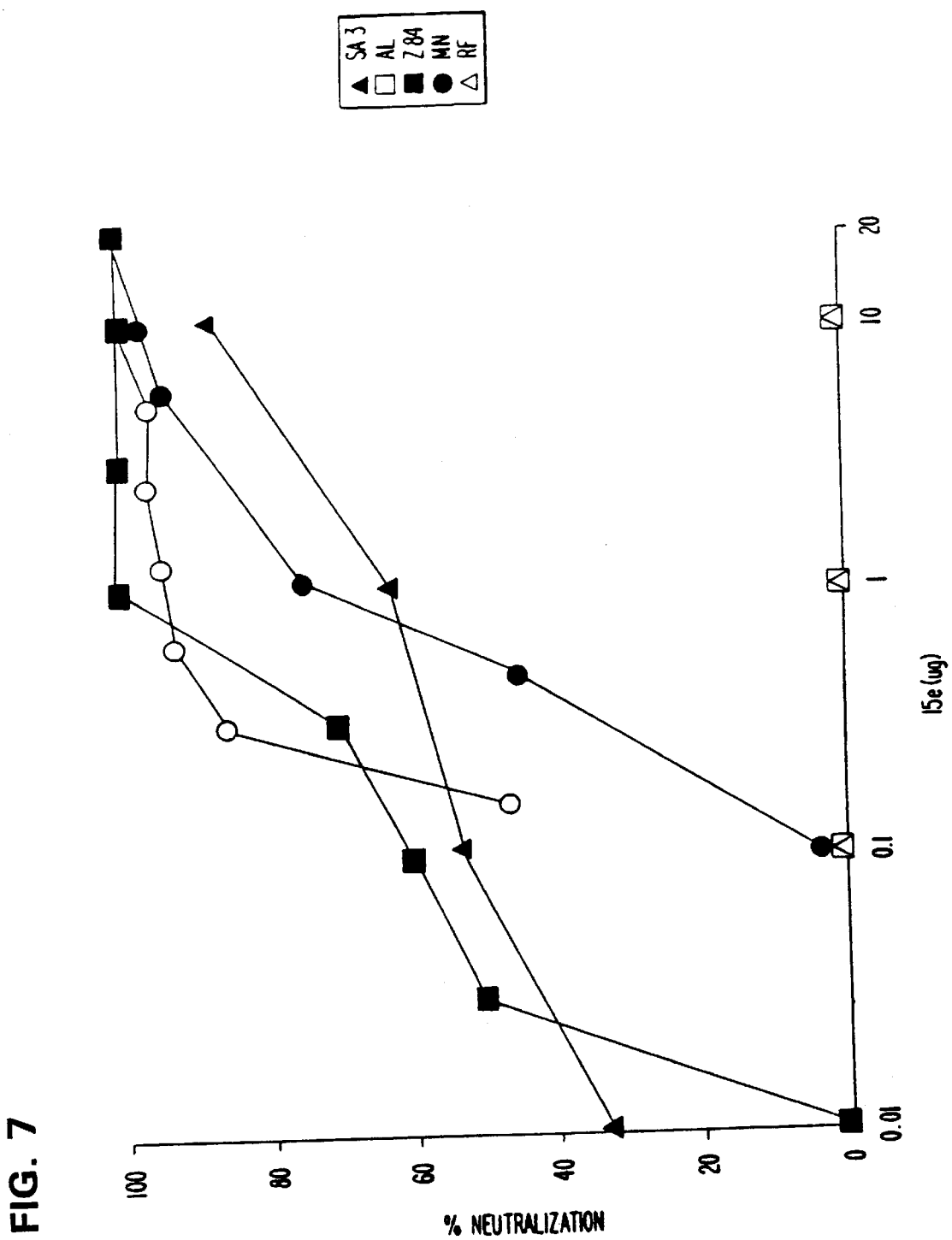

FIG. 7 demonstrates I5e neutralization of diverse HIV-1 isolates: —O—, IIIB; -__-, RF; ■, Z84; Cl, AL; ●, MN; ▲,, SA3.

Figure 8:
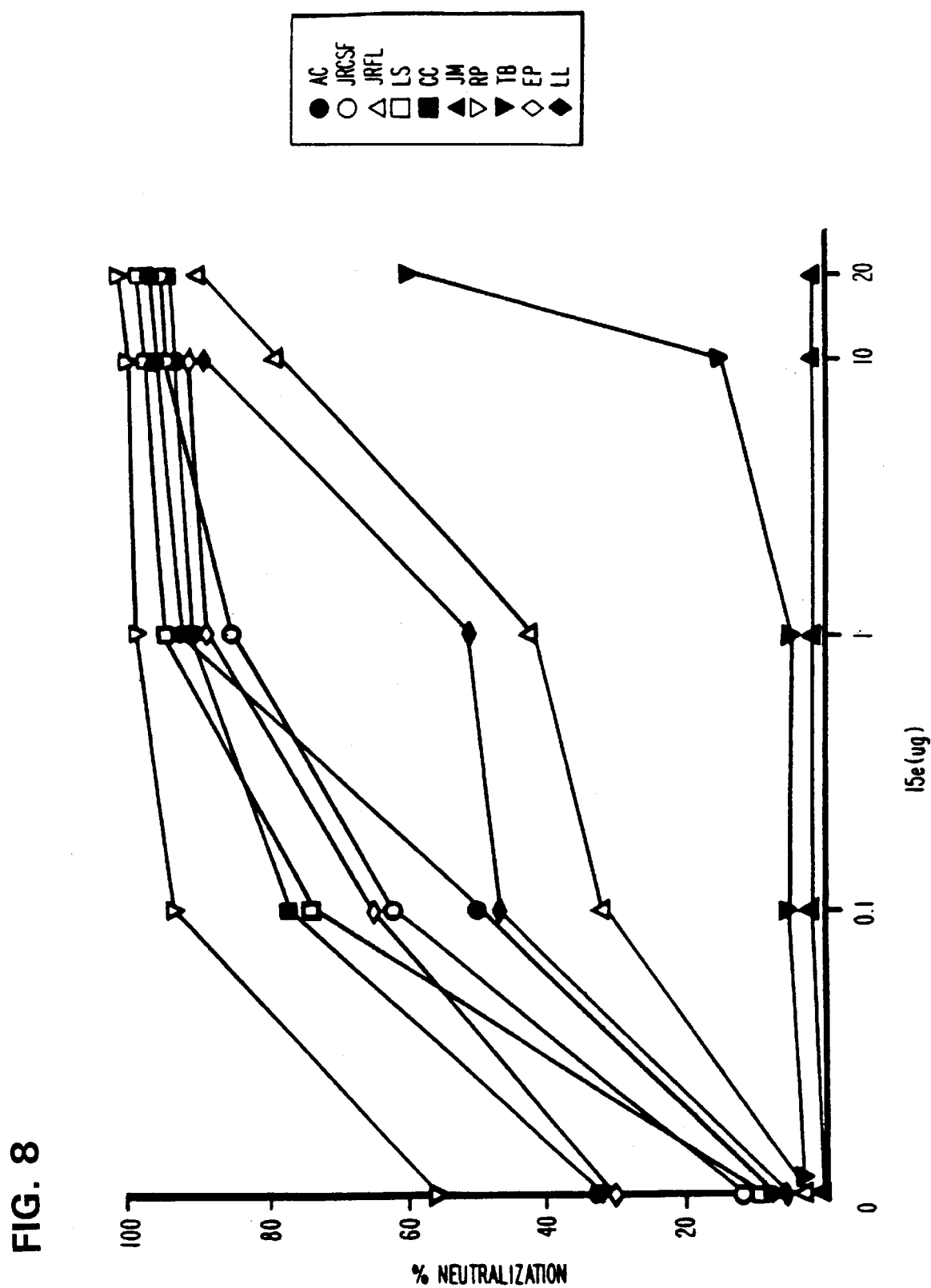

FIG. 8 displays I5e neutralization of nine out of ten primary HIV isolates. Note the variable potency. ●, AC, °, JRCSF; __, JRFL; □, LS, ■, CC; ▲,, JM; __,RP; ∀,, TB; ◇, EP; ♦, LL.

Figure 9:
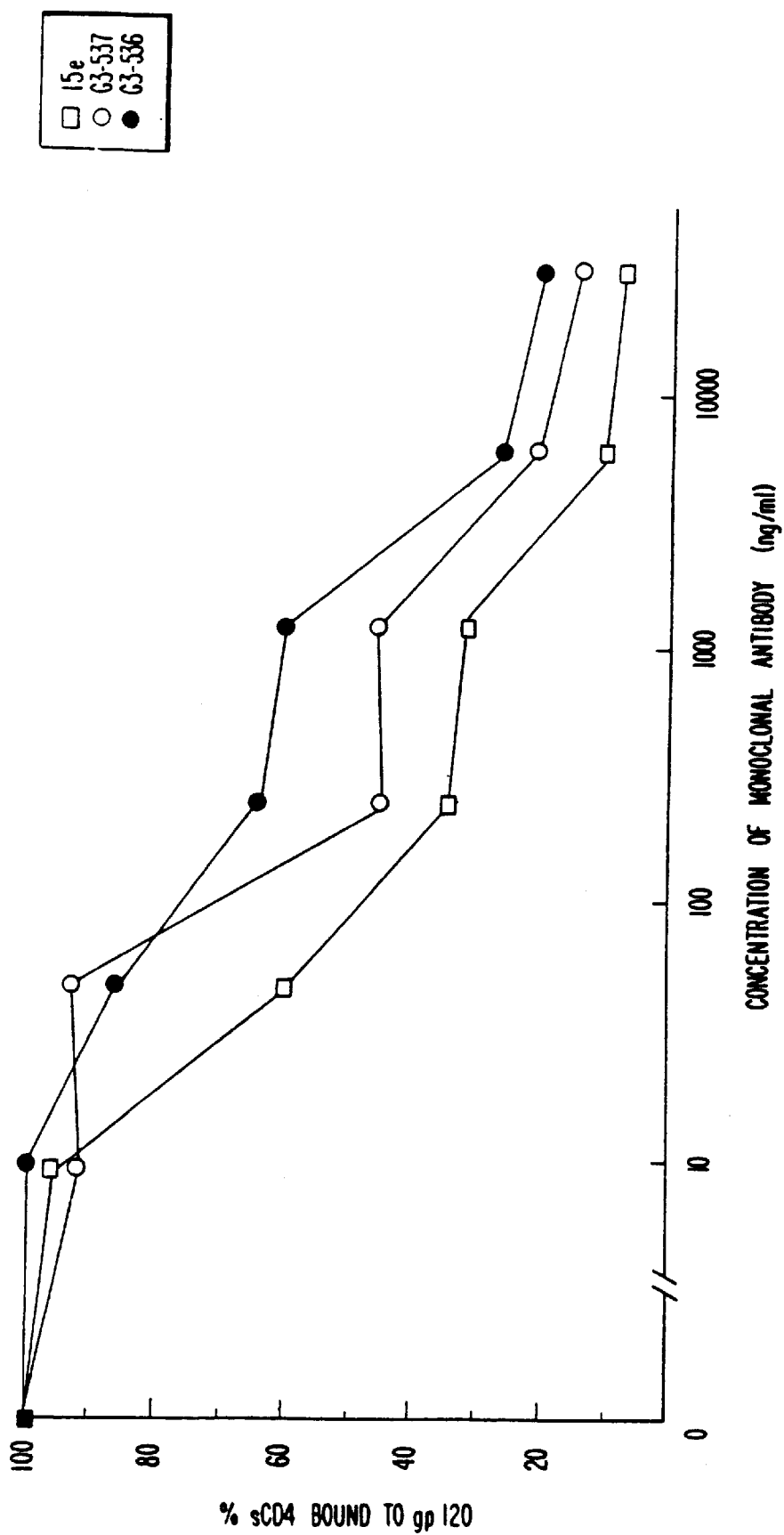

FIG. 9 illustrates that I5e blocks CD4-gp120 binding more efficaciously than HMab directed against the epitope described by Lasky et al.

Figure 10A:
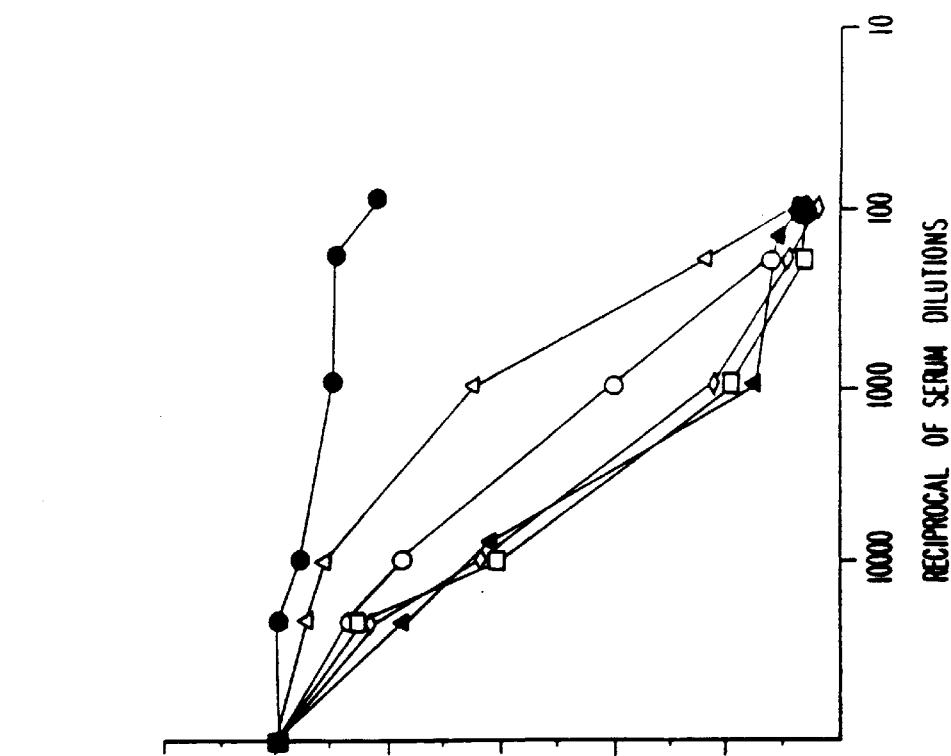
Figure 10B:
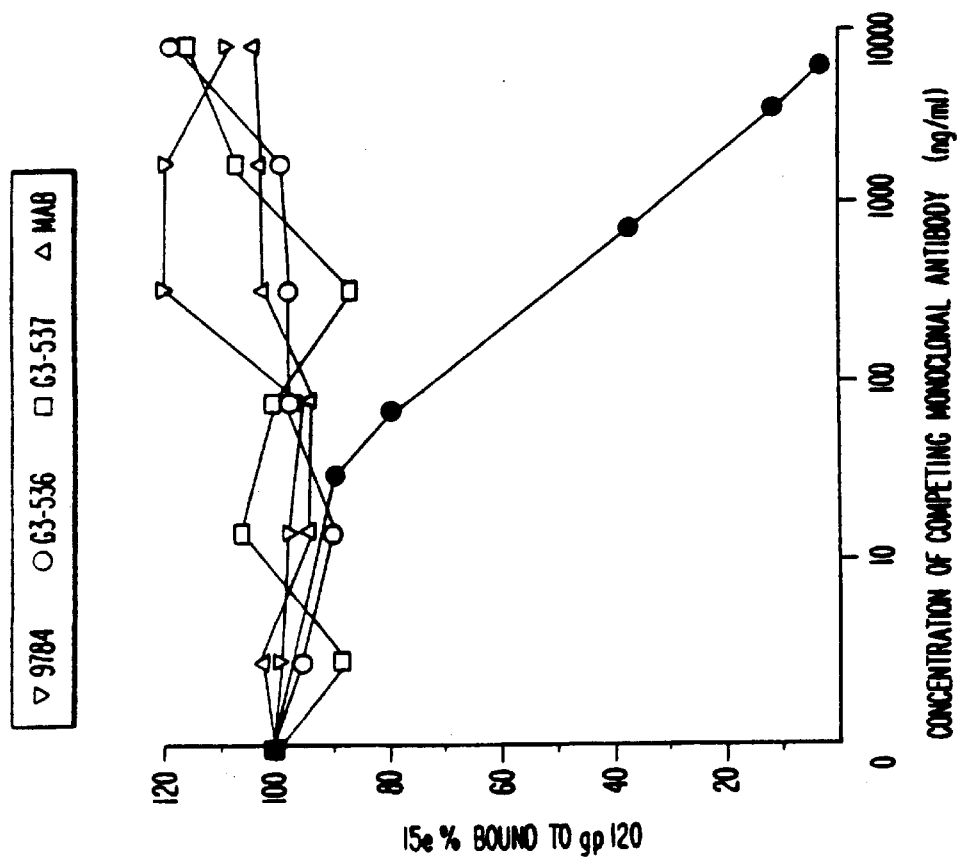

FIGS. 10A and 10B provide further proof that the I5e binding site is novel. In particular, FIG. 10 shows competition for I5e bindine to gp120 by [A] other anti-gp120 MAbms: 9784 (__; directed against the V3 loop of gp120), G3-536 (°), G3-537 (□), and G3-136 (__); and by [B]1 normal human serum (●) and HIV-1-positive human sera (__, °, ▲,, □).

In FIG. 10A, no competition is observed between I5e and antibodies directed at previously described epitopes (i.e., "loop," NH₃-terminus, and the Lasky site)

FIG. 10B shows the competitive inhibition of I5e binding by sera obtained from six AIDS patients. Competitive inhibition of I5e occurred with convalescent sera, but not with the sera from acute seroconverters. It is believed that I5e inhibitory antibodies develop approximately six-twelve months after initial HIV seroconversion.

Figure 11:
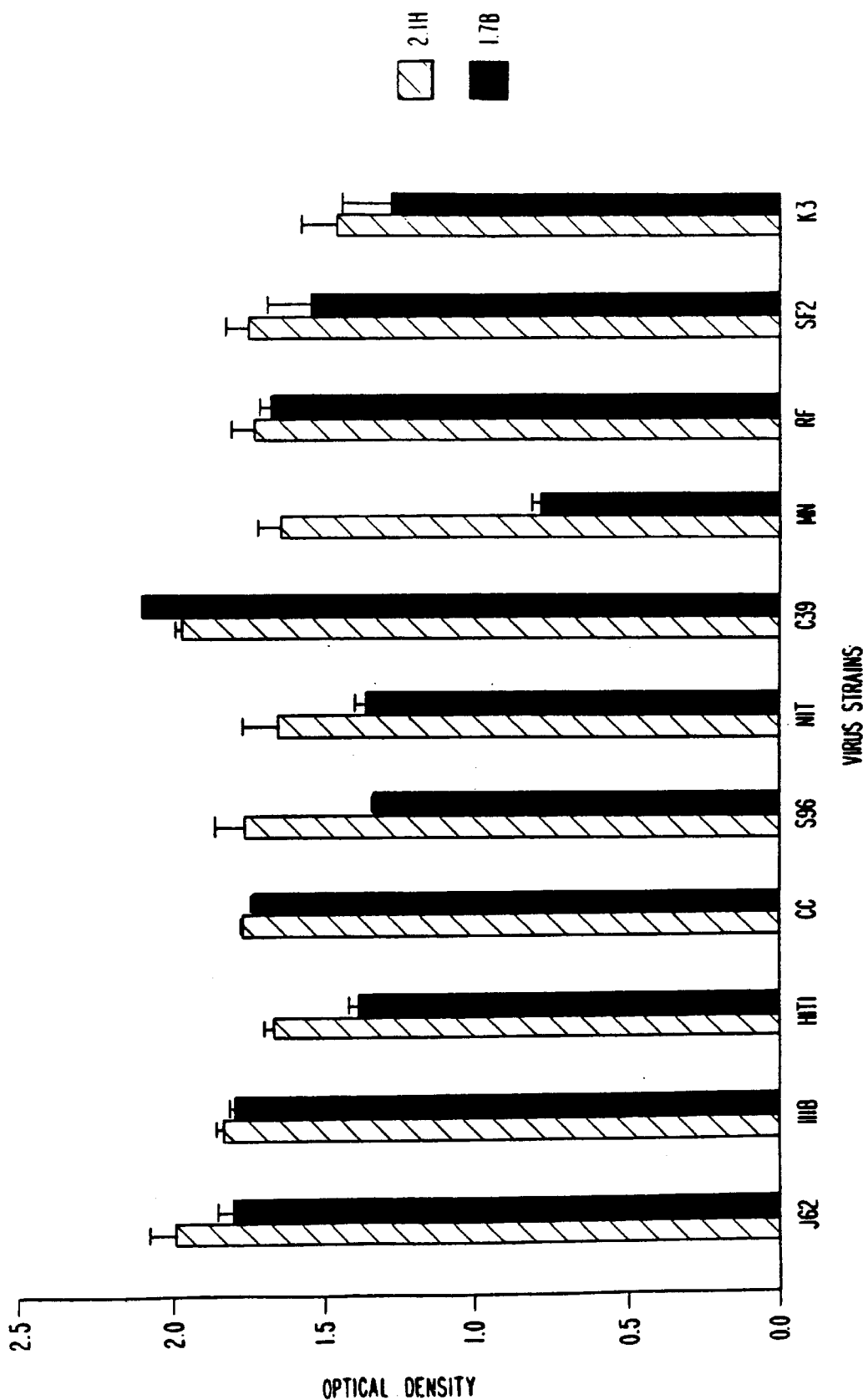

FIG. 11 is a graphic representation of ELISA reactivity of N70-1.7B and N70-2.0H HMabs with Con-A immobilized gp120 from eleven strains of HIV-1. Results are shown as the mean O.D. from triplicate determinations. Standard deviation bars are shown.

5. DETAILED DESCRIPTION

A. Production Of Human Monoclonal Antibodies (HMabs)

The following examples and procedures are provided to illustrate the methods for obtaining antibodies, derivatives thereof, and their use. They are not, however, intended to limit the invention, which extends to the full scope of the appended claims.

i. Epstein-Barr Virus Transformation

Peripheral blood mononuclear cells (PEMC) from three adult HIV-1 seropositive male subjects were isolated on Ficoll-Hypaque gradients. PBMC were depleted of CD3 positive T cells using an indirect panning technique (20) in which cells reacting with the OKT3 monoclonal antibody were absorbed to petri dishes coated with F(ab)$_2$ antibodies to mouse IgG. Non-adherent cells, enriched in B cells, were inoculated with the B95-8 strain of EBV (21) and plated at $10^3$ or $10^4$ cells per well in ninety-six well tissue culture plates with irradiated human umbilical cord blood lymphocytes (HUCL, $10^5$ cells per well) as feeder cells. Cultures were maintained in RPMI 1640 containing 5% fetal calf serum (FCS) and 1% Nutridoma-HU (Boehringer-Mannheim), a serum substitute of low protein content.

ii. ELISA

Two methods were used to immobilize HIV-1 antigens in wells of ELISA plates for antibody screening. In one system, HIV-1 infected H9 cells were immobilized in Concanavalin-A (Con-A) coated assay wells and then fixed with 1:1 acetone-methanol. The wells were blocked with RPMI-10% FCS for one hour. Fluids from ninety-six well cultures were transferred to wells in the assay plates. After one hour, wells were washed with phosphate buffered saline (PBS) containing 0.1% Triton-X 100 (PBS-Tx) and then reacted with peroxidase-conjugated antibody to human IgG (Protos Labs). Color was developed with 100 µl tetramethylbenzidine (TMB)-H$_2$O$_2$ as substrate. The reaction was stopped by the addition of H$_2$SO$_4$ and color was read as Optical Density (O.D.) at 450 nm in a Titertek Multiskan ELISA reader.

The other ELISA method was a novel immunoassay based on the observation that HIV envelope glycoproteins bind via their carbohydrate moieties to Con-A (22). In this system, wells of Immulon-2 assay plates (Dynatech) were coated with 200 µl/ml Con-A in PBS. The wells were then incubated with 100 µl of detergent disrupted supernatant fluids from HIV-1 producer cell lines grown for two-three days in serum free RPMI supplemented with 1% Nutridoma-Hu. In the absence of serum components, disrupted viral glycoproteins present in such culture fluids bind to Con-A in amounts sufficient to function as solid phase antigens in a highly sensitive ELISA. Unreacted Con-A binding sites were blocked with RPMI-10% FCS for one hour. Control antigens were similarly prepared from culture fluids of uninfected MT4 cells. Transformed B cell culture fluids were transferred to both antigen coated and control wells of assay plates which were incubated at room temperature for one hour. Binding of antibodies was measured as in the first assay. This ELISA was also used in later experiments to test the reactivity of HMabs with glycoproteins from different virus strains.

iii. HIV Strains

Eleven HIV-1 strains were used in these studies. Strains C39, J62, SA90, SA96, and L86 were isolated in our laboratory from mitogen activated T cells of five asymptomatic HIV-1 infected subjects by co-cultivation with activated normal T cells in medium supplemented with Interleukin-2 (IL-2). Strain SA3 was similarly isolated in our laboratory from a patient with AIDS; strain HiTi (23) was obtained from Robert Garry, Tulane Medical School; strain K3 was obtained from S.R.S. Rangan of the Tulane Delta Primate Center; HTLV-IIIB (24), the prototype HIV-1 strain, was obtained from American Type Culture Collection; HTLV-III$_{MN}$ (25–26), as well as glycosylated recombinant gp120 from HIV-1$_{SF2}$ (27), was obtained from AIDS Research and Reference Reagent Program. Strains C39, J62, SA96, and SA90 were grown in MT4 cells (28); HTLV-IIIB, HTLC-III$_{MN}$, SA3, HiTi, and K3 were grown in H9 cells. Strain L86, isolated from the B cell donor of one monoclonal antibody (K24-3B), did not replicate in continuous T cell lines and was propagated in mitogen activated cord blood T cells in medium containing one hundred units per ml recombinant IL-2. To prepare antigens for Con-A immobilization, cells infected with each virus strain were grown for two-three days in serum free medium RPMI supplemented with 1% Nutridoma-HU. Clarified fluids were treated with 1% Triton-X and stored in aliquots at −20° C. until use.

iv. Western Blot and Dot Blot Assays

Extracts of 1–2×10$^7$ HIV-1 infected cells prepared by solubilizing cells for thirty minutes in 1% Triton-X followed by removal of insoluble material by centrifugation in a microcentrifuge. Samples were mixed 1:1 with sodium dodecyl sulfate (SDS) sample buffer without reducing agents and heated for 5 min at 90° C. Cell lysates of uninfected H9 and MT4 cells were similarly prepared. Samples were fractionated by electrophoresis in 7.5% sodium dodecyl sulfate-polyacrylamide gels in a BioRad mini-gel apparatus. Proteins were then electrophoretically transferred to a nitrocellulose membrane. Western blot strips were incubated with blocking buffer (1% bovine serum albumin, 0.5% Tween 20, in 0.5 M NaCl, 10 mM Tris, pH 8), reacted first with each antibody preparation, and then with alkaline phosphatase-conjugated antibodies to human or sheep IgG, as appropriate. Colored bands were developed using nitroblue tetrazolium and 5-bromo-4-chloro-3-indolyl-phosphate (NBT-BCIP) as substrate. A sheep antiserum to gp120 of HTLV-IIIB, obtained from the AIDS Research and Reference Reagent Program, was used as positive control in detecting gp120/160.

For dot blot assays, strips of nitrocellulose were dotted with 1 μl of baculovirus-produced, recombinant LAV gp120 at 100 μl/ml and J62 envelope glycoproteins, which were partially purified from detergent treated serum-free culture medium by lentil lectin affinity chromatography (22) and concentrated to 10 μl/ml. Recombinant gp120 was also dotted after being heated for five minutes at 95° C. in the presence or absence 2-mercaptoethanol. Antibody assays on dot blot strips were performed as for Western blots, except a goat antiserum to gp160 of HTLV-IIIB (29) was used as a positive control.

V. Isolation of Antibody Producing B Cell Lines

In the first transformation experiment, EBV exposed-T cell-depleted PBMC from an HIV-1 infected donor were plated at 10$^3$ cells per well in ninety-six well culture plates with irradiated HUCL feeder cells. Only about 50% of the cultures were transformed after four-five weeks of culture. Culture fluids were screened by ELISA for IgG antibodies reacting with fixed, immobilized HIV infected H9 cells. One transformed culture, designated K24-3b, was a stable producer of an antibody, which on further testing reacted by indirect immunofluorescence with both fixed and unfixed HIV-1 infected cells but not with uninfected cells. Multiple subcultures of K24-3b cells were established at low cell density and all continued to produce antibody. We were unable to definitively clone K24-3b and after about eight months all subcultures ceased to grow; but by that time we accumulated about one liter of antibody containing culture medium. Because the original cells were plated at a relatively low cell density and the incidence of transformation was less than 50%, it is likely that the K24-3b cell line was established as a clone.

In the second experiment, EBV exposed-T cell-depleted PBMC from another HIV positive subject were seeded at 10$^4$ cells/well with irradiated HUCL in two ninety-six well plates. Transformation occurred in 100% of the wells. Culture fluids were screened by ELISA for IgG antibodies reacting with Con-A immobilized viral glycoproteins derived from the J62 strain of HIV-1 grown in MT4 cells in serum free medium. Ten transformed cultures produced IgG antibodies reacting with J62 glycoproteins but not with control antigen. Seven cultures produced antibodies for less than two months. Three cell lines, designated N70-2.3a, N70-1.5e, and N70-1.9b, respectively, were stable antibody producers and were cloned at ten cells per well.

The IgG subclass and light chain type of four of the antibodies was determined by reactivity with murine monoclonal antibodies to the four heavy chain subclasses (Behring Diagnostics) or polyclonal goat antibodies to lambda and kappa light chains in a sandwich ELISA. These four HMabs are of the IgG1 subclass; K24.3b, N70-1.5e, and N70-1.9b contain kappa light chains and N70-2.3a contains lambda light chains. Isotyping of the three more recently produced HMabs, N70-1.7B, N70-2.H and Y76-4.8D has not yet been performed. However, we believe them to be also of the IgG1 subclass because of their binding affinity to gp120.

vi. Characterization of HMab Specificity by Western Blot and Dot Blot Assays

Figure 1A:
Figure 1B:
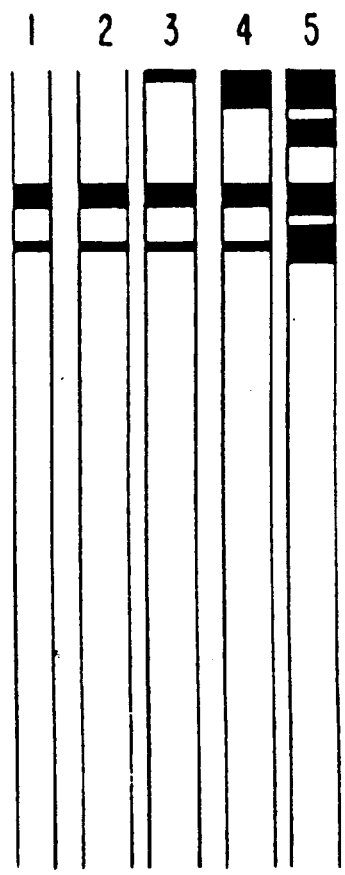

FIG. 1 shows the reactivity of four of the HMabs on Western blots of antigens of two HIV-1 strains, HTLV-IIIB and J62. On blots of HTLV-IIIB (Panel A) three HMabs (K24-3B, N70-2.3a, and N70-1.5e) reacted strongly with a prominent band of approximately 120 kd and with a less intense band of 160 kd. Although N70-1.9b appeared to react weakly with gp120 on this blot (Panel A, lane 4), in other assays it did not react with HTLV-IIIB. On blots prepared from strain J62 (Panel B), all four HMabs showed identical binding to a prominent band at 160 kd below which was a diffuse band extending to approximately 120 kd. This diffuse band pattern is characteristic for this strain. The staining patterns obtained with a polyclonal sheep antibody to gp120 on blots of both strains were identical to that observed with the monoclonals (Panels A and B, lane 5). The HMabs did not react with blots of uninfected MT4 or H9 cells.

Figure 2:
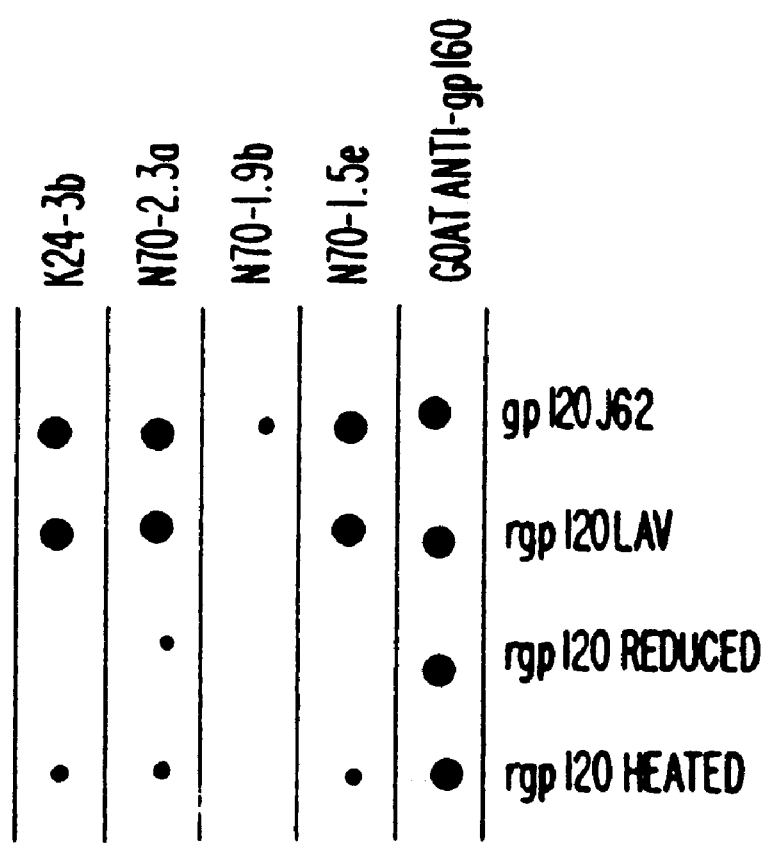

While these results appeared to indicate that these four HMabs react with gp120 and its uncleaved cellular precursor, gp160, Zolla-Pazner et al (30) recently presented evidence that bands identified as gp160/120 in some commercially available HIV-1 Western blot strips are multimers of gp41. Therefore, to further confirm that the four HMabs are indeed specific for gp120, we tested their binding on dot blots of recombinant LAV gp120 and lentil lectin purified J62 glycoproteins. As shown in FIG. 2, three of the four HMabs (K24-3b, N70-2.3 and N70-1.5e) reacted strongly with recombinant gp120. N70-1.9b did not bind to LAV gp120 but did bind to J62 antigen. The amount of J62 antigen dotted was about ten fold less than the recombinant antigen, explaining the weaker staining observed with this antigen. These results, therefore, indicate that the bands of 120 and 160 kd observed on our Western blots indeed represent gp120/160.

In additional Western blot studies, neither K24-3b nor N70-2.3a reacted with blots prepared from cell lysates heated in sample buffer containing 2-mercaptoethanol, suggesting that the epitopes identified were sensitive to reduction. To further test the effect of reduction on these epitopes, the antibodies were tested on dot blots of recombinant gp120 LAV that were heated at 95° C. in the presence or absence of 2-mercaptoethanol. The results shown in FIG. 2 demonstrate that K24-3b and N70-1.5e did not bind to reduced antigen, that binding of N70-2.3a to reduced antigen was significantly diminished, and that heating alone only slightly diminished the antigenic activity of these antibodies. As N70-1.9b did not bind to LAV gp120, the effect of reduction on its epitope was not determined in this experiment. We have subsequently tested N70-1.9 on dot blots of reduced and non-reduced J62 glycoproteins and observed no reactivity with reduced antigen. (Unpublished data.) Thus, all four HMabs identify reduction sensitive epitopes.

vii. Analysis of Strain Specificity of HMabs by ELISA

Figure 3:
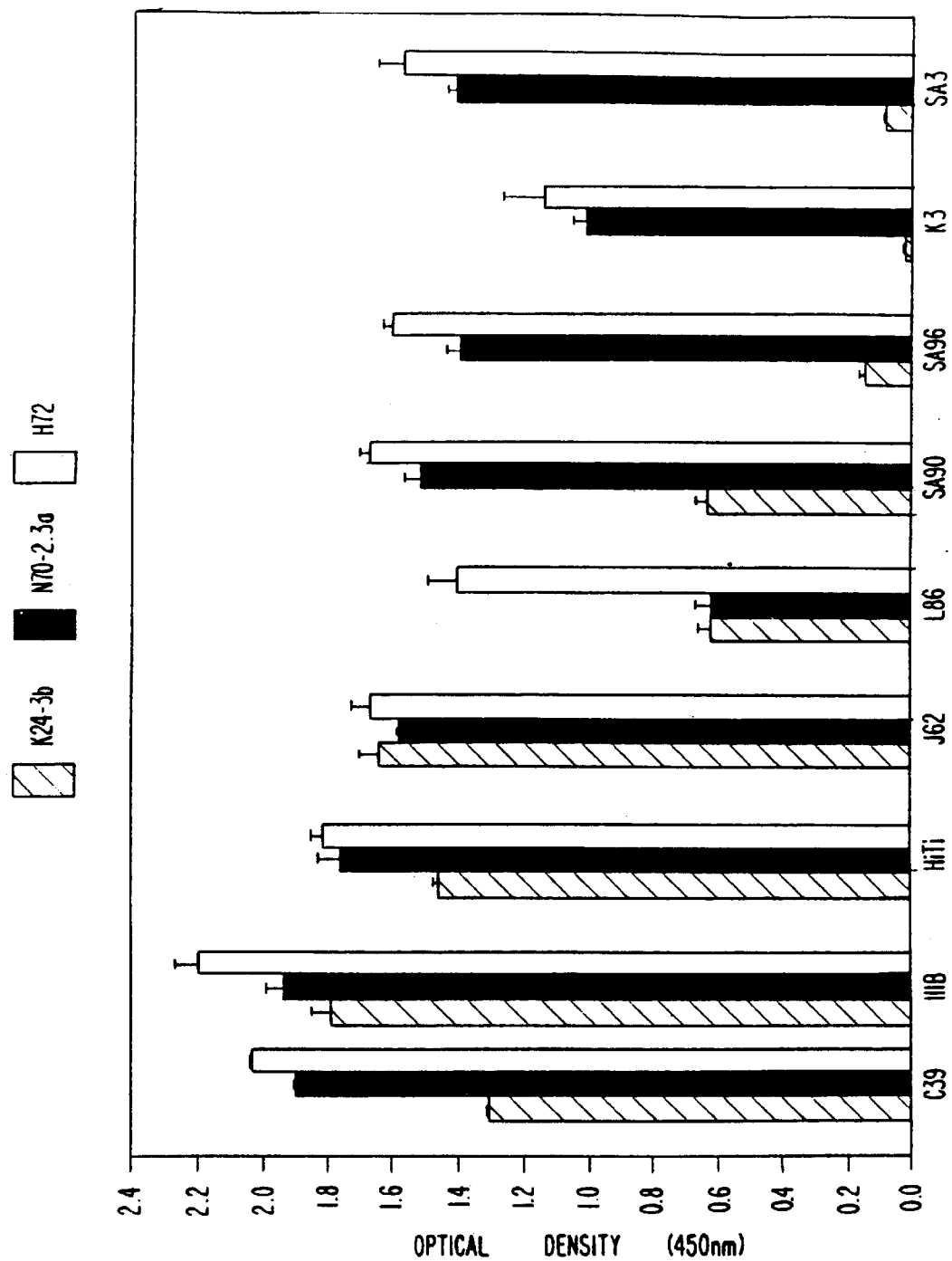

The four HMabs tested previously were also tested by ELISA for reactivity with Con-A immobilized viral glycoproteins from different HIV-1 strains. In one experiment (FIG. 3) culture fluids of K24-3b and N70-2.3a, and a HIV-1 positive control serum (H72) were tested on a panel of nine different strains, which included L86, the strain isolated from the B cell donor of K24-3b. Antibody N70-2.3a reacted with all nine strains. Although some differences in binding of this antibody on the panel were observed, generally parallel differences were observed with the positive control serum. Thus, it is likely that the binding levels of both N70-2.3a and the H72 serum provide a relative measure of the amounts of gp120 immobilized from each strain. We have no explanation for the much weaker reactivity of N70-2.3a with the L86 strain compared to the positive serum. However, L86 was the only strain grown in IL-2 dependent primary T cells, which release less virus than continuous cell lines. Possibly more gp41 than gp120 was immobilized in the L86 virus preparation and antibodies to gp41 account for the greater serum reactivity.

By comparison to N70-2.3, the K24-3b monoclonal showed remarkable variability in reactivity with these viruses. This antibody reacted with six of the nine strains but did not bind to strains SA3 or K3, and showed minimal binding to strain SA96. Whereas the reactivity of both N70-2.3a and K24-3b with strains L86 and J62 were very nearly the same, the binding of K24-3b to strains SA90 and C39 was much less than N70-2.3a, the difference being greatest with SA90. These observations have been reproducible in assays performed with different batches of antigens. Smaller differences in binding of these two antibodies were also apparent with strains HiTi and HTLV-III. These differences were not related to antibody concentrations, since preparations of both antibodies used in these assays appeared to saturate available antigenic sites on immobilized antigens; and optical densities obtained with serial dilutions of both antibodies up to 1:32 were very nearly the same (data not shown) when tested against the J62 isolate. This data appears to indicate that N70-2.3a identifies a conserved epitope, while K24-3b identifies a variant epitope which is heterogeneously expressed in this panel of virus strains.

Figure 4:
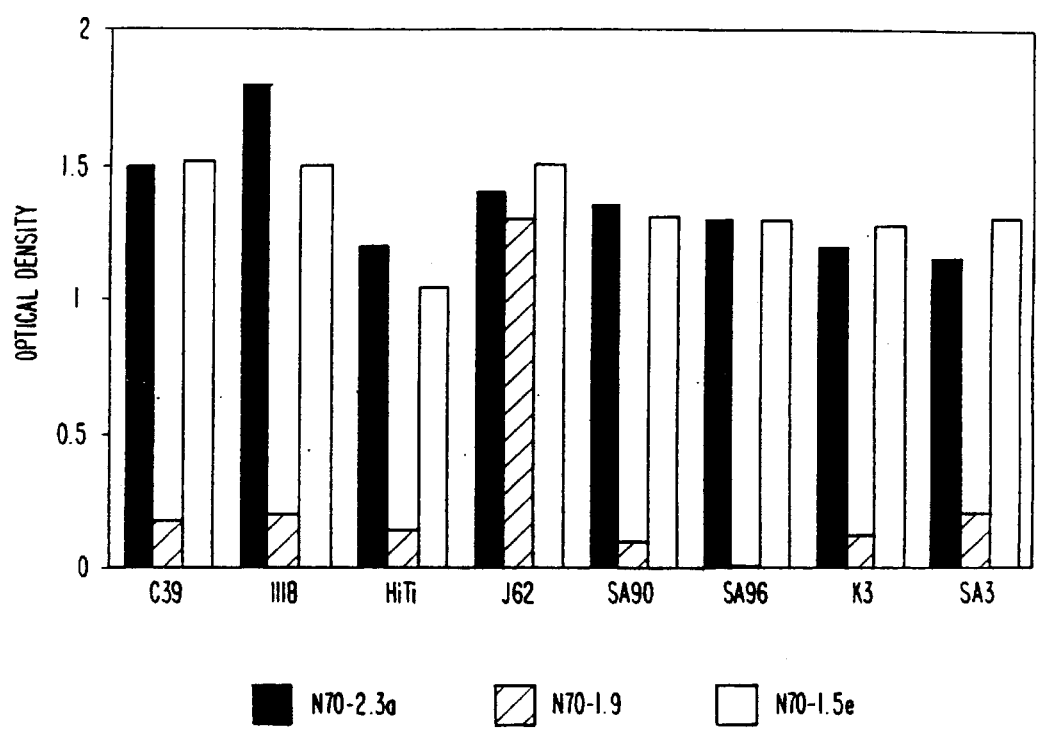

FIG. 4 illustrates the results of a similar experiment comparing the reactivities of N70-1.9b with Con-A immobilized glycoproteins derived from eight strains. In this experiment, N70-2.3a served as a positive control. Whereas, both N70-1.5e and N70-2.3a reacted strongly with all eight strains, N70-1.9b reacted only with J62, the strain that was used in screening the original B cell cultures for antibody production. The results indicate that N70-1.5e, like N70-2.3a, reacts with an epitope shared by all strains tested thus far, while N70-1.9b reacts with a strain-restricted epitope. However, in a subsequent experiment, we found that N70-1.9b, as well as the other three HMabs, reacted strongly by ELISA with Con-A immobilized glycoproteins from two other strains, HTLV-III$_{MN}$, and HIV-1$_{SF2}$. These findings, which are presented in Table I below, indicate that the N70-1.9b defined epitope is not as highly strain restricted as the results in FIG. 5 initially suggested.

TABLE I

Reactivity of Four HMabs with Con-A Immobilized gp120 of Three HIV-1 Strains

| HMab | Optical Density with Indicated Strain | | |
|---|---|---|---|
| | HTLV-III$_{MN}$ | rgp120/HIV-I | J62 |
| K24-3b | 1.870 | 0.681 | 1.882 |
| N70-2.3a | 2.018 | 1.149 | 2.007 |
| N70-1.5e | 1.924 | 1.648 | 1.781 |
| N70-1.9b | 1.710 | 1.307 | 1.397 |

To summarize thus far, our data appear to indicate that N70-2.3a and N70-1.5e both identify a conserved epitope, while K24-3b and N70-1.9b (to a lesser extent) appear to identify a variant epitope heterogeneously expressed in a panel of virus strains. Moreover, all four HMabs identify reduction sensitive epitopes.

viii. Strain Specificity of HMabs by Western Blot Analysis

Figure 5A:
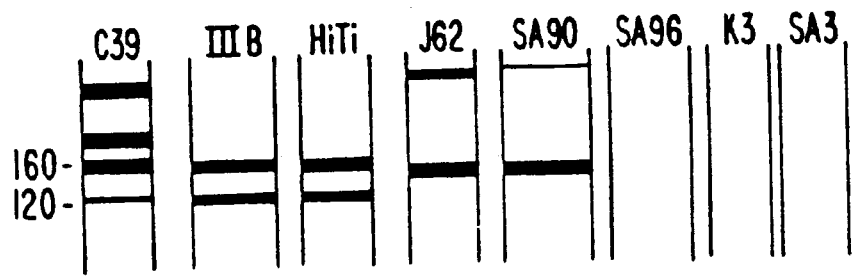
Figure 5B:
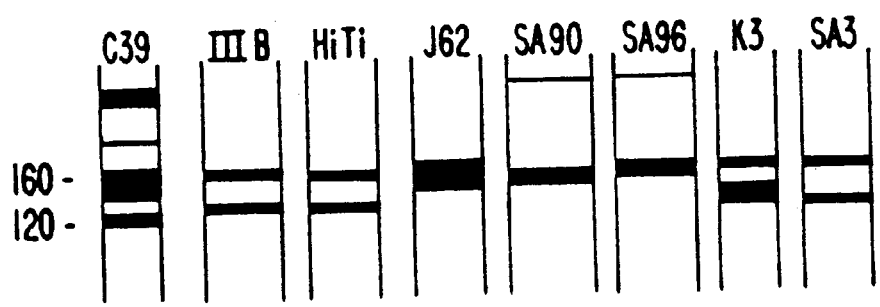

The strain specificity of two of the four HMabs, K24-3b and N70-2.3a, were also tested on Western blots prepared from the panel of HIV-1 strains identified above. The results, shown in FIG. 5, are in agreement with results obtained by ELISA. Antibody N70-2.3a reacted with gp120/160 from all eight strains. Antibody K24-ob reacted with gp120/160 from the same strains it identified by ELISA. Similarly, K24-3b failed to react with SA3 and K3; and its minimal reactivity with strain SA96 was below the sensitivity of photography. Although N70-1.5e and t70-1.9b have not been similarly tested by Western blots on all viruses, the strain restricted reactivity of N70-1.9b, as observed by ELISA, is corroborated by its failure to react with recombinant LAV gp120 in dot blot assays.

ix. HMab N70-1.5e (I5e), The Prototype And The Best Mode Antibody

We consider the I5e HMab to be the prototype because it was the first antibody discovered having specificity for a conformation dependent epitope involved in gp120 -CD4 binding. Since then, we have generated three additional HMabs, N70-1.7B, N70-2.1H and Y76-4.8D, which each have I5e-like characteristics. These three new Hmabs are still under investigation; however, preliminary data with respect to their neutralization and binding capacity is presented in Section x. below. In the meantime, the I5e HMab was studied in greater detail, employing routine laboratory procedures. (For lab procedures, see: References 16, 37 and 41.) Our findings in this subsequent series of tests is as follows.

In a radio-immunoprecipitation assay, which results are illustrated in FIG. 6A, I5e proved to be reactive with gp120 and/or its precursor gp160 from HIV-1 isolates IIIB, MN and Z84, but not with RF and AL.

I5e was also tested for neutralizing activity against multiple laboratory and primary HIV-1 isolates and shown to have broad neutralizing specificity. As illustrated in FIGS. 7 and 8, HMab I5e exhibited in vitro neutralization activity against four of five laboratory isolates of HIV and nine of ten primary HIV isolates. More importantly, the efficacy of I5e neutralization of these isolates can be realized by their relatively low ID$_{50}$ and ID$_{90}$ values. In FIG. 7, I5e neutralized laboratory isolates IIIB, Z84, MN and SA3 with 90% inhibitory doses (the dose required to inhibit activity by 90%; LD$_{90}$) of 0.4, 0.6, 3.5, and 12.0 ug, respectively. Isolates RF and AL were refractory to neutralization by I5e, which is consistent with the immunoprecipitation results in FIG. 6. The neutralization assay was performed as described previously (16, 37, 41), with the p24 antigen concentration in the supernatant used as the indicator of virus infection.

Briefly, as described in Ho et al. Science 1988, 50% tissue culture infective doses of HIV were incubated with serial dilutions of the test serum for 1 hour at 37° C. before inoculation onto $2 \times 10^6$ H9 cells. Viral expression was subsequently determined on day 7 of culture, and neutralization was defined as >90% reduction both in syncytia formation and in the amount of p24 antigen in supernatant, as compared to controls.

This procedure is also described in Ho et al. Journal of Virology 1987, where HIV-neutralizing assays were performed using he H9 clone as the target cells and the HTLV-IIIB isolate as the virus inoculum. Cell-free HIV was harvested from a chronically infected H9 culture and titrated on uninfected H9 cells, and the titer was expressed as 50% tissue culture infective dose per milliliter. Each virus inoculum (100 µl, 50 50% tissue Culture infective doses) was preincubated with test serum or immunoglobulin preparation (100 µl, serial twofold dilutions) for 1 h at 37° C. before inoculation onto $2.0 \times 2 \times 10^6$ H9 cells in 5 ml of RPMI 1640 medium supplemented with fetal calf serum (20%), HEPES (N-2-hydroxyethylpiperazine-N'-2-ethanesulfonic acid)(10 mM), penicillin (250 U/ml), streptomycin (250 µl/ml), and L-glutamine (2 mM). On days 7 through 10, each culture was examined for characteristic cytopathic effects with syncytia formation and for reverse transcriptase activity in the supernatant fluid. Neutralization was defined as the complete inhibition of syncytia formation and >90% reduction in reverse transcriptase activity compared with control cultures, which were similarly established except that the virus inoculum was preincubated with culture medium or seronegative control human serum. HIV serum neutralizing titers of 1:4 or greater were considered positive.

A similar procedure is described in Sun et al. Journal of Virology 1989. It describes a neutralization assay in which 100 µl of virus inoculum (50 50% tissue culture infective doses) was preincubated with 100 µl of test antibodies of different concentrations for 1 h at 37° C. before inoculation into $0.75 \times 10^6$ H9 cells in 1.5 ml of RPMI 1640 medium supplemented with 15% fetal bovine serum, 10 mM HEPES (N-2-hydroxyethylpiperazine-N'-2-ethanesulfonic acid), 250 U of penicillin per ml, 250 µg of streptomycin per ml, and 2 mM L-glutamine. On day 7, cell-free culture supernatants were collected for assay of HIV-specific p24 antigen by ELISA.

FIG. 8 demonstrates the neutralizing capacity of I5e against ten primary HIV-1 isolates. As illlustrated, six primary strains were efficiently neutralized, with an $ID_{90}$ of less than 1.5 ug, while more I5e was required to neutralize three other strains, and one isolate was completely resistant. These results attest to the great potency and broad specificity of I5e in neutralizing HIV isolates, and are summarized in tabular form in Table II below.

TABLE II

| | 15E Neutralization | |
|---|---|---|
| | $ID_{50}$(ug) | $ID_{90}$(ug) |
| Lab Strains: | | |
| IIIB | 0.15 | 0.4 |
| Z34 | 0.03 | 0.6 |
| MN | 0.50 | 3.5 |
| RF | >20.0 | >20 |

TABLE II-continued

| | 15E Neutralization | |
|---|---|---|
| | $ID_{50}$(ug) | $ID_{90}$(ug) |
| AL | >20.0 | >20 |
| SA3 | 0.10 | >10 |
| Clinical Isolates: | | |
| AC | 0.10 | 0.60 |
| JRCSF | 0.06 | 1.50 |
| JRFL | 1.50 | 10.5 |
| LS | 0.04 | 0.40 |
| CC | 0.01 | 0.50 |
| JM | >20.0 | >20.0 |
| RP | <0.01 | 0.07 |
| TB | 15.0 | >20.0 |
| EP | 0.05 | 0.90 |
| LL | 1.00 | 10.0 |

We next examined I5e for its ability to compete with CD4 for gp120/gp160 binding, as this is one potential mechanism for the HIV-1 neutralizing activity. In the experiment shown in FIG. 6B, increasing doses of sCD4 were added to a metabolically labelled lysate of HIV-1 prior to immunoprecipitation. Soluble CD4 competed with I5e in a dose dependent manner, suggesting that the epitope on gp120 for this human monoclonal antibody may be on the surface, which makes contact with CD4. This observation was confirmed by a quantitative competition enzyme immunoassay, with recombinant gp120 captured indirectly onto solid-phase and sCD4. As shown in FIG. 9, I5e blocked gp120-sCD4 binding in a dose-dependent manner. In fact, it was more potent in doing so than two mouse anti-gp120 monoclonal antibodies, G3-536 and G3-537, previously mapped to the putative CD4-binding site described by Lasky et al. (17). The amount of I5e, G3-536 and G3-537 required to reduce gp120-sCD4 binding by 50% was 70, 2,500 and 200 ng/ml, respectively. Further epitope classification studies, as illustrated in FIG. 10A, indicated that the I5e epitope does not overlap any previously described epitope, including the "loop," the $NH_3$-terminus and the Lasky site.

Together, these findings suggest that the epitope of I5e is probably not composed of a linear sequence. Instead, the epitope is likely to be conformation or carbohydrate dependent or both. The conformational nature of the I5e epitope was confirmed by the studies shown in FIG. 6C. After reduction of a metabolically labeled lysate of HIV-1 by 0.1 M dithiothreitol, the gp120/gp160 reactivity of I5e was lost. Similarly, the importance of glycosylation to I5e-gp120 reactivity was confirmed by the studies shown in FIG. 6D, where metabolically labeled HIV-1 lysates were prepared in the absence and presence of tunicamycin. The unglycosylated enveloped precursor polypeptide of 90 kD was not recognized by I5e, perhaps because of alterations in the tertiary structure. Alternatively, it is possible that an oligosaccharide moiety contribues directly to form a part of the I5e epitope. In any event, these findings suggest that I5e epitope is not localized to previously defined functional domains of gp120 and is likely to be a novel site important in both CD4 binding and antibody neutralization of HIV-1.

Neutralization activity was also observed more broadly across various sera from primary HIV isolates than with lab isolates. Furthermore, as shown in FIG. 10B, it was observed that sera from HIV infected patients competitively inhibited I5e binding, whereas sera from acute seroconverters did not. This finding suggests that the I5e binding site may be responsible for inducing the broad neutralizing and binding inhibitory activity observed in convalescent human sera (six to twelve months after initial HIV seroconversion). TABLE III below represents I5e reactivity with a number of HIV isolates.

TABLE III

| Peptide Antigen | HIV-1 Isolate | Amino Acid No. | Source | Enzyme Immunoassay O.D. | Results |
|---|---|---|---|---|---|
| gp120 | IIIB | 29–511 | purified (NIH) | 1.212 | + |
| rgp120 | SF2 | 28–509 | recomb., CHO (Chiron) | 1.096 | + |
| rgp120 | | | recomb., CHO (Chiron) | 1.162 | + |
| rgp120 | | | recomb., baculo (Chiron) | 0.321 | − |
| rgp120 | | | recomb., E. coli (Chiron) | 0.051 | − |
| env2-3 | SP2 | 28–509 | recomb., yeast (Chiron) | 0.089 | − |
| PE3 | HXB2 | 1–287 | recomb., E. coli (Dupont) | 0.107 | − |
| PB1 | HXB2 | 288–463 | recomb., E. coli (Repligen) | 0.046 | − |
| PEnv9 | HXB2 | 464–511* | recomb., E. coli (Dupont) | 0.041 | − |
| C1 | HXB2 | 85–100 | synthetic (Tanox) | 0.023 | − |
| R13 | HXB2 | 174–188 | synthetic (Tanox) | 0.033 | − |
| C2-1 | HXB2 | 197–213 | synthetic (Tanox) | 0.035 | − |
| C2-2 | HXB2 | 209–223 | synthetic (Tanox) | 0.025 | − |
| C2-3 | HXB2 | 219–233 | synthetic (Tanox) | 0.028 | − |
| C2-4 | HXB2 | 229–243 | synthetic (Tanox) | 0.030 | − |
| C2-5 | HXB2 | 239–253 | synthetic (Tanox) | 0.030 | − |
| C2-6 | HXB2 | 249–263 | synthetic (Tanox) | 0.027 | − |
| C2-7 | HXB2 | 259–273 | synthetic (Tanox) | 0.028 | − |
| V3-2 | HXB2 | 308–322 | synthetic (Tanox) | 0.047 | − |
| C3-1 (T35S) | HXB2 | 413–447 | synthetic (Tanox) | 0.031 | − |
| R11 | HXB2 | 430–439 | synthetic (Tanox) | 0.021 | − |
| I | Bru | 430–439 | synthetic (Tanox) | 0.022 | − |
| II | Bru | 432–441 | synthetic (Tanox) | 0.027 | − |
| III | Bru | 434–443 | synthetic (Tanox) | 0.024 | − |
| IV | Bru | 436–445 | synthetic (Tanox) | 0.027 | − |
| V | Bru | 438–447 | synthetic (Tanox) | 0.021 | − |
| VI | Bru | 440–449 | synthetic (Tanox) | 0.019 | − |
| 44 | Bru | 430–449 | synthetic (Tanox) | 0.030 | − |
| P4 | HXB2 | 451–477 | synthetic (Tanox) | 0.071 | − |
| P3 | HXB2 | 466–477 | synthetic (Tanox) | 0.029 | − |
| P2 | HXB2 | 476–492 | synthetic (Tanox) | 0.025 | − |
| P1 | HXB2 | 489–512 | synthetic (Tanox) | 0.025 | − | x. HMABs N70-1.7B, N70-2.1H And Y76-4.8D

Since the discovery of HMab I5e, we have produced three new HMabs exhibiting I5e-like activity. All three were generated by EBV transformation of B cells. While N70-1.7B and N70-2.1H were derived from B cells obtained from the same patient from whom I5e was derived, HMab Y76-4.8D was derived from a different patient.

We initiated our examination of these HMabs by testing the strain specificity of HMabs N70-2.1H and N70-1.7B by ELISA for reactivity with Con-A immobilized viral glycoproteins from eleven different HIV-1 strains. Our results are illustrated in FIG. 11 and Table IV. As FIG. 11 shows, HMab N70-2.1H demonstrated particularly strong reactivity with all eleven strains in the panel. HMab N70-1.7B showed similar strong activity, reacting with ten of eleven strains; the MN strain being the only non-reactive strain. In Table IV, the third HMab, Y76-4.8D, was shown to have similar I5e-like behavior; although weaker reactivity was seen with the RF and SF2 strains. However, these results constitute merely preliminary data; whether any of the newly produced antibodies is better than I5e with respect to neutralization remains to be determined by further experimentation.

TABLE IV

Comparison of Strain Specificity of HMabs 4.8D and 1.5e

| Virus Strain | OD with Indicated HMab | |
|---|---|---|
| | 4.8D | 1.5e |
| J62 | 1.562 | 1.857 |
| HiTi | 1.714 | 1.962 |
| IIIB | 1.893 | 2.002 |
| MN | 1.453 | 2.049 |
| RF | .717 | .568 |
| SF2 | .562 | 1.714 |

We next examined the three new HMabs for their ability to compete with each other for the same or overlapping epitopes on gp120. In this experiment, gp120 of HIV-1 strain J62 was immobilized in wells of an Immulon II assay plate (Dynatech Laboratories) which were coated with HMab N70-1.9b at 10 ug/ml PBS for one hour. The wells were reacted with each unlabeled HMab (Competing Antibody), and then with either biotinylated N70-2.3a or biotinylated N70-1.5e. The relative amount of bound biotin—labeled antibody was determined by incubating peroxidase—streptavidin (Boeringher-Mannheim) in the wells and developing color using TMB-$H_2O_2$. Optical density was read at 450 nm.

As shown in Table V, low O.D. readings for the unlabeled antibodies, as compared to the control O.D. for each biotin-HMab, indicates that an unlabeled HMab competes for an antigenic site which overlaps the site recognized by labeled antibody. As illustrated, N70-2.3a competes with biotin-2.3a but not with biotin-1.5e. In contrast, N70-1.5e, N70-1.7B, N70-2.1H and Y76-4.8D all have low O.D. readings for biotin-1.5e, indicating that all compete with N70-1.5e.

TABLE V

Competition of HMabs with Biotinylated HMabs 2.3a and 1.5e

| Competing Antibody | OD with Indicated Labeled HMab | |
|---|---|---|
| | Biotin-2.3 | Biotin-1.5e |
| 2.3a | .115 | 1.071 |
| 1.5e | 1.313 | .135 |
| 1.7B | 1.496 | .432 |
| 2.1H | 1.580 | .129 |
| 4.8D | 1.209 | .455 |
| None | 1.101 | 1.102 |

In FIGS. 6B and 9, we established that I5e recognizes an epitope involved in gp120-CD4 binding. As a result, we were interested in determining whether the new HMab N70-2.1H also recognized an epitope involved in gp120-CD4 binding. In this experiment, three concentrations of srCD4 (10 ug/ml, 5 ug/ml and 2.5 ug/ml) were incubated with gp120 of HIV-1$_{J62}$ immobilized in Con-A coated wells. HMabs N70-2.3a, N70-1.5e and N70-2.1H were added to the wells and their binding determined using the peroxidase-anti-human IgG system as described previously. As shown in Table VI, srCD4 had no effect on the binding of N70-2.3a. However, srCD4 at all concentrations tested, significantly dimished the binding of both N70-1.5e and N70-2.1H. Hence, it appears that N70-2.1H, like N70-1.5e, also recognizes an epitope involved in gp120-CD4 binding.

TABLE VI

Competition of HMabs with Soluble rCD4

| HMab | Optical Density with Indicated Concentration of CD4 | | | |
|---|---|---|---|---|
| | 10 ug/ml | 5 ug/ml | 2.5 ug/ml | None |
| 2.3A | 1.460 | 1.371 | 1.386 | 1.263 |
| 1.5E | .272 | .413 | .447 | 1.061 |
| 2.1H | .404 | .476 | .466 | .856 |

B. Discussion Of Working Examples Of The Preferred Embodiment

We disclose the production of six IgG HMabs with specificity for gp120/160 to HIV-1 by B cell lines derived by EBV transformation of peripheral blood B cells obtained from three asymptomatic HIV-1 infected patients. Five HMabs (N70-2.3a, N70-1.5e, N70-1.7B, N70-2.1H and Y76-4.BD) bind to epitopes shared by the majority of strains tested thus far, and therefore, tentatively identify well conserved epitopes. The sixth antibody, (K24-3b), binds to variant epitopes, identifying an epitope that is absent in 2 virus strains and heterogeneously expressed in 9 other strains. Together these results demonstrate the feasibility of using HMab production by EBV transformed cells to probe human antibody responses to both variant and conserved epitopes of gp120 that are immunogenic in chronically infected hosts.

With regard to the biological activities of the HMabs, preliminary studies have indicated that N70-1.5e has surprisingly potent neutralizing activity against HTLV-IIIB, even at antibody concentrations as low as 1 µg/ml. (For neutralization procedures, see reference 37.) However, whether any of the newly generated antibodies has broader or more effective neutralizing capacity than I5e remains to be determined. Of interest is the fact that I5e did not bind to gp120 of the RF and AL strains. As FIG. 11 illustrates, N70-2.1H appeared to bind all strains tested, including RF; and could therefore have broader activity if, in further experiments, it proves to neutralize as well as I5e. Similarly, N70-1.7B appeared to bind to RF, but did not bind the MN strain; and could also have potentially broader activity if it neutralizes as well as I5e. Experiments have also shown that these antibodies mediate antibody dependent cell-mediated cytotoxicity (ADCC) against target cells expressing gp120/160.

C. The Deposit

A sample of the N70-1.5e cell line was deposited with the American Type Culture Collection (ATCC) 10801 University Boulevard, Manassas, Va. 20110-2209 on May 25, 1990 and assigned Accession No. CRL10464. A sample of the N70-2.1H cell line was also deposited with the ATCC on May 23, 1991 and assigned Accession No. CRL10758.

We have deposited a sample of the N70-1.5e cell line, what we consider to be the prototype and our best mode, and a sample of the N70-2.1H cell line with the ATCC in order to afford permanence of the deposit and ready accessibility to the public if a patent is granted. All restrictions on the availability of the deposited N70-1.5e and N70-2.1H cell lines will be irrevocably removed upon the grant of a patent. Moreover, these cell lines will be available during the pendency of this application, as determined by the Commissioner, pursuant to 37 C.F.R. § 1.15 and 35 U.S.C. § 122. We also acknowledge our duty to replace either or both of the deposits during the required term of deposit, should the ATCC be unable to furnish a sample when requested due to the condition of either or both deposits.

BIBLIOGRAPHY

1. Hahn B M, Gonda M A, Shaw G M, et al: Genomic diversity of the acquired immunodeficiency syndrome virus HTLV-III: different viruses exhibit greatest divergence in their envelope genes. Proc Natl Acad Sci (USA) 1985; 82:4813–4817.
2. Starich B R, Hahn B H, Shaw G M, et al: Identification and characterization of conserved and variable regions in the envelope gene of HTLV-III/LAV, the retroviruses of AIDS. Cell 1986; 45:637–648.
3. Modrow S, Hahn, B H, Shaw G M, et al: Computer assisted analysis of envelope protein sequences of seven human immunodeficiency virus isolates: predictions of antigenic epitopes in conserved and variable regions. J. Virol 1987; 61:570–578.
4. Hahn B H, Shaw G M, Taylor M E, et al: Genetic variation in HTLV-III/LAV over time in patients with AIDS or at risk for AIDS. Science 1986; 232:1548–1554.
5. Weiss R A, Clapham P R, Cheingsong-Popov R. et al: Variable and conserved neutralization antigens of human immunodeficiency virus. Nature (London) 1986; 324:572–575.
6. Matthews T J, Langlois A J, Robey W J, et al: Restricted neutralization of divergent human T-lymphotropic virus type III isolates by antibodies to the major envelope glycoprotein. Proc Natl Acad Sci (USA) 1986;83:9709–9713.
7. Nara P L, Robey W G, Pyle S W, et al: Purified envelope glycoproteins from human immunodeficiency virus type I variants induce individual, type specific neutralizing antibodies. J Virol 1988; 62:2622–2628.

8. Palker T J, Clark M E, Langloise A J, et al: Type-specific neutralization of the human immunodeficiency virus with antibodies to env-encoded synthetic peptides. Proc Natl Acad Sci (USA) 1988;85;1932–1936.
9. Rusche J R, Javaherian K, McDanal C, et al: Antibodies that inhibit fusion of human immunodeficiency virus-infected cells bind to a 24 amino acid sequence of the viral envelope, gp120. Proc Natl Acad Sci (USA) 1988; 85:3198–3202.
10. Matsushita S, Robert-Guroff M, Rusche J, et al: Characterization of a human immunodeficiency virus neutralizing monoclonal antibody and mapping of the neutralizing epitope. J. Virol. 1988; 62:2107–2114.
11. Skinner M A, Ting R. Langlois A J, et al: Characteristics of a neutralizing monoclonal antibody to the HIV envelope glycoprotein. AIDS Research and Human Retroviruses 1988; 4:187–197.
12. Skinner M A, Langlois A J, McDanal C B, et al: Neutralizing antibodies to an immunodominant envelope sequence do not prevent gp120 binding to CD4. J Virol 1988; 62:4195–4200.
13. Linsley P S, Ledbetter J A, Kinney-Thomas E, and Hu S L: Effects of anti-gp120 monoclonal antibodies on CD4 receptor binding by the env protein of human immunodeficiency virus type 1. J Virol 1988; 62:3695–3702.
14. Lasky L A, Nakamura G, Smith D, et al: Delineation of a region of the human immunodeficiency virus type 1 gp120 glycoprotein critical for interaction with CD4 receptor. Cell 1987; 50:975–985.
15. Dowbenko D, Nakamura G, Fennie C et al: Epitope mapping of the human immunodeficiency virus type 1 gp120 with monoclonal antibodies. J Virol 1988; 62:4703–4711.
16. Ho D, Sarngadharam M G, Hirsch M S et al: Human immunodeficiency virus neutralizing antibodies recognize several conserved domains on the envelope glycoproteins. J Virol. 1987; 61:2024–2028.
17. Robert-Guroff M, Brown M, and Gallo, RC: HTLV-III neutralizing antibodies in patients with AIDS and AIDS-related complex. Nature 1985; 316:72–74.
18. Harada S, Kobayashi N, Koyanagi Y, and Yamamoto N: Clonal selection of human immunodeficiency virus (HIV): serological differences in the envelope antigens of the cloned viruses and HIV prototypes (HTLV-IIIB, LAV, and ARV). Virology 1987; 156:447–451.
19. Cheng-Mayer C, Homsy J, Evans L A, and Levy J A: Identification of Human immunodeficiency virus subtypes with distinct patterns of sensitivity to serum neutralization. Proc Natl Acad Sci (USA) 1988; 85:2815–2819.
20. Wysocki, L J and Sato, V L: Depletion of lymphocyte subsets by panning. Proc Natl Acad Sci (USA) 1980; 75:2844–2848.
21. Miller, G. and Lipman M: Release of Infectious Epstein-Barr virus by transformed marmoset leukocytes. Proc Natl Acad Sci (USA) 1973; 70:190–194.
22. Montagnier L, Clavel F, Krust B, et al: Identification and antigenicity of the major envelope glycoprotein of lymphadenopathy-associated virus. Virology 1985; 144:283–289.
23. Rasheed S, Gottlieb A A, and Garry R F: Cell killing by ultraviolet-inactivated human immunodeficiency virus. Virology 1986; 154:395–400.
24. Popovic M, Sarngadharan M G, Read E and Gallo R C: Detection, isolation, and continuous production cytopathic retroviruses (HTLV-III) from patients with AIDS and pre-AIDS. Science 1984; 224:497–500.
25. Gallo R C, Salahuddin S Z, Popovic M, Shearer G M et al: Frequent detection and isolation of cytopathic retroviruses (HTLV-III) from patients with AIDS and at risk for AIDS. Science 1984; 224:500–502.
26. Shaw G M, Hahn B H, Arya S K, Groopman J E et al: Molecular characterization of human T cell leukemia (lymphotropic) virus type III in the acquired immunodeficiency syndrome. Science 1984; 226:1165–1170.
27. Levy J A, Hoffman A D, Kramer S M, et al: Isolation of Lymphocytopathic retroviruses from San Francisco patients with AIDS. Science 1984; 225:840–842.
28. Harada S., Koyanagi Y, and Yamamoto N: Infection of HTLV-III/LAV in HTLV-I carrying cells MT-2 and Mt-4 and application in a plaque assay. Science 1985; 229:563–566.
29. Rusche J R, Lynn D L, Robert-Guroff M, et al: Humoral immune response to the entire human immunodeficiency virus envelope glycoprotein made in insect cells. Proc Natl Acad Sci (USA) 1987; 84:6924–6926.
30. Zolla-Pazner S, Gorny M K, and Honnen W J: Reinterpretation of human immunodeficiency virus western blot patterns. New Engl J Med 1989; 320:1280–1281.
31. Banapour B, Rosenthal K, Rabin L, et al: Characterization and epitope mapping of a human monoclonal antibody reactive with the envelope glycoprotein of human immunodeficiency virus. J Immunol 1987; 139:4027–4033
32. Sugano S, Masuho Y, Matsumoto Y, et al: Human monoclonal antibody against glycoproteins of human immunodeficiency virus. Biochem and Biophys Res Commun 1988; 155:1105-1112.
33. Morrow W J W, Gaston I, Sooy C D and Levy J A: Human monoclonal antibody directed against gag gene products of the human immunodeficiency virus. J. Immunol. 1988; 140:941–943.
34. Gorny M K, Gianakako V, Sharpe S and Zolla-Pazner S: Generation of Human monoclonal antibodies to human immunodeficiency virus. Proc Natl Acad Sci (USA) 1989; 86:1624–1628.
35. Amadori A, Ciminale V, Calabro M L, et al: Human monoclonal against a gag-coded protein of human immunodeficiency virus produced by a stable EBV-transformed cell clone. AIDS Research and Human Retroviruses 1989; 5:73–78.
36. Yarchoan R, Redfield R R, and Broder S: Mechanisms of B cell activation in patients with acquired immunodeficiency syndrome and related disorders. J. Clin Invest. 1986; 78:439–447.
37. Ho D D, Kaplan J C, Rackauskas I E, and Gurney M E: Second conserved domain of gp120 is important to HIV infectivity and antibody neutralization. Science 1988; 239:1021–1023.
38. Takeda A, Tuason C U and Ennis F A: Antibody-enhanced infection by HIV-1 via Fc receptor-mediated entry. Science 1988; 242:580–583.
39. Chou M J, Less T H, Hatsakis A, et al: Antibody responses in early human immunodeficiency virus type 1 infection in hemophiliacs. J Inf Dis. 1988; 157:805–811.
40. Cheng-Mayer C, Seto D, Masatoshi T, and Levy J A: Biologic features of HIV-1 that correlate with virulence in the host. Science 1988; 240:80–82.
41. Sun N C, Ho D D, Sun C R Y, Liou R S, Gordon W, Fund M S C, Li L, Ting R C, Lee T H, Chang N T, Chang T W: Generation and characterization of monoclonal antibodies to the putative CD4-binding domain of HIV-1 gp120 . J. Virol., 1989; 63:3579–3585.
42. Haigwood, N L, Barker, C B, Higgins, K W et al.: Evidence for neutralizing antibodies directed against conformational epitopes on HIV-1 gp120 . Vaccines 1990; 90:313–320.

We claim:

1. A method for determining the efficacy of a monoclonal antibody to neutralize primary isolates of Human Immunodeficiency Virus Type 1, said method comprising the steps of:

providing a known concentration of H9 cells in a first receptacle, a second receptacle, a third receptacle, a fourth receptacle, and a fifth receptacle, wherein all five receptacles comprise the same concentration of H9 cells for inoculation;

providing a primary HIV-1 isolate;

adding fifty percent tissue culture infective doses of the primary HIV-1 isolate to four increasing concentrations of the monoclonal antibody, whereby resulting in four different mixtures of primary HIV-1 isolate and monoclonal antibody, wherein each mixture is contained in a separate container, and wherein the monoclonal antibody is selected from the group consisting of monoclonal antibodies produced by the cell line deposited with the ATCC under Accession No. CRL10758 and monoclonal antibodies produced by the cell line deposited with the ATCC under Accession No. CRL10464;

inoculating the H9 cells of four of the five receptacles with the four different mixtures of primary HIV-1 isolate and monoclonal antibody, wherein each receptacle receives a mixture from only one container, whereby resulting in four different cultures;

providing one control culture by adding a fifty percent tissue culture infective dose of the primary HIV-1 isolate to the fifth receptacle containing only H9 cells;

preparing a supernatant from each of the four cultures and the one control culture, whereby resulting in five supernatants;

determining the concentration of p24 antigen in each of the five supernatants, wherein the p24 antigen concentration is used as an indicator of virus infection; and determining the efficacy of the antibody to neutralize HIV infection by comparing the concentration of p24 antigen in each of the five supernatants.

* * * * *